(12) United States Patent
Weber et al.

(10) Patent No.: US 7,135,006 B1
(45) Date of Patent: Nov. 14, 2006

(54) FINGER POSITIONER

(75) Inventors: James J. Weber, Santa Barbara, CA (US); Michael J. Berman, Santa Barbara, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 0 days.

(21) Appl. No.: 11/047,529

(22) Filed: Feb. 1, 2005

(51) Int. Cl.
*A61F 5/00* (2006.01)
(52) U.S. Cl. ............................................ 602/22; 602/5
(58) Field of Classification Search .................... 602/5, 602/22, 30, 21; 2/21, 161.7, 16; D24/190
See application file for complete search history.

(56) References Cited

U.S. PATENT DOCUMENTS

| | | | | |
|---|---|---|---|---|
| 1,315,035 A | * | 9/1919 | Post | 606/237 |
| 5,513,657 A | * | 5/1996 | Nelson | 128/879 |
| 2003/0191421 A1 | * | 10/2003 | Weaver et al. | 602/22 |

* cited by examiner

*Primary Examiner*—Henry Bennett
*Assistant Examiner*—Camtu Nguyen
(74) *Attorney, Agent, or Firm*—William W. Haefliger

(57) ABSTRACT

A positioner to control the position of a finger or thumb of the hand, comprising an elongated, flexible holder configured to extend along the upper side of the user's finger or thumb; a retainer carried by the holder to retain the tip of the user's finger or thumb, the holder adapted to be anchored, remotely from the retainer, endwise thereof; the holder configured to flex, thereby allowing bending of the finger or thumb, producing tensioning of the holder that resists such bending.

20 Claims, 4 Drawing Sheets

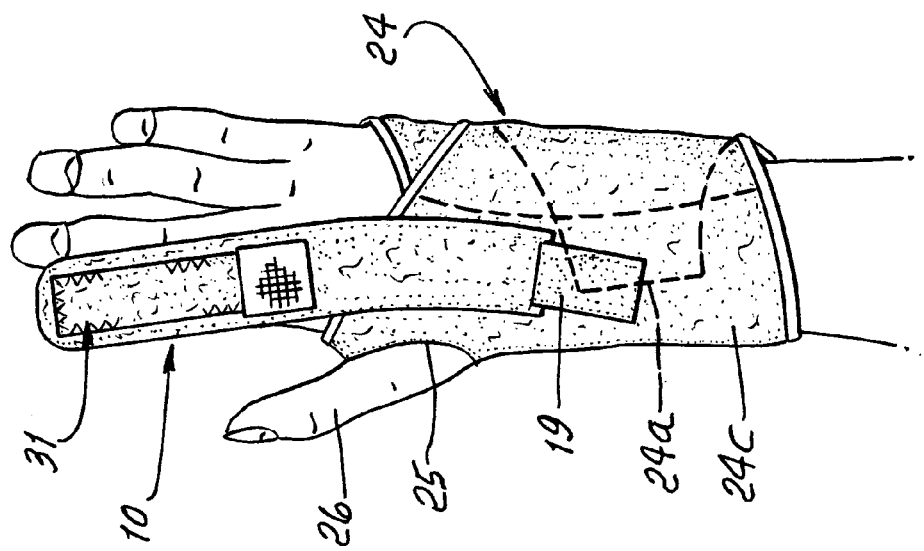
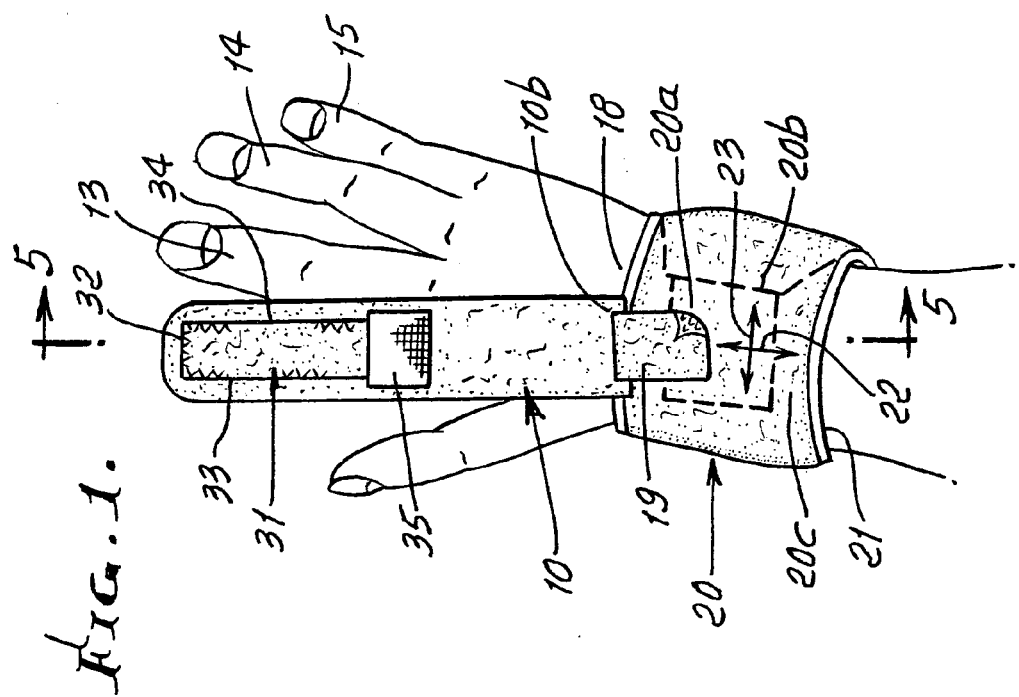

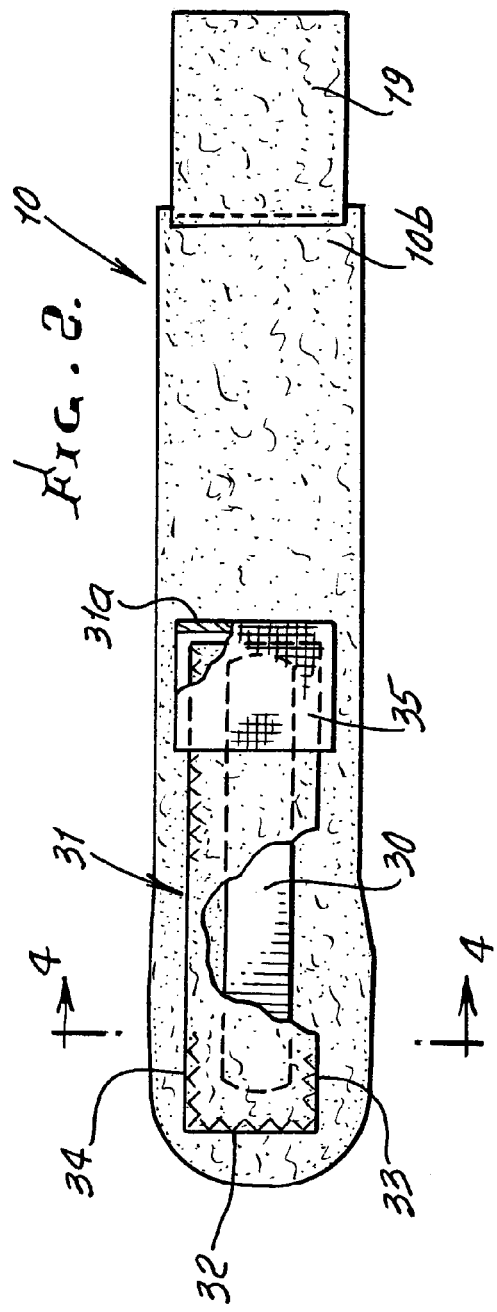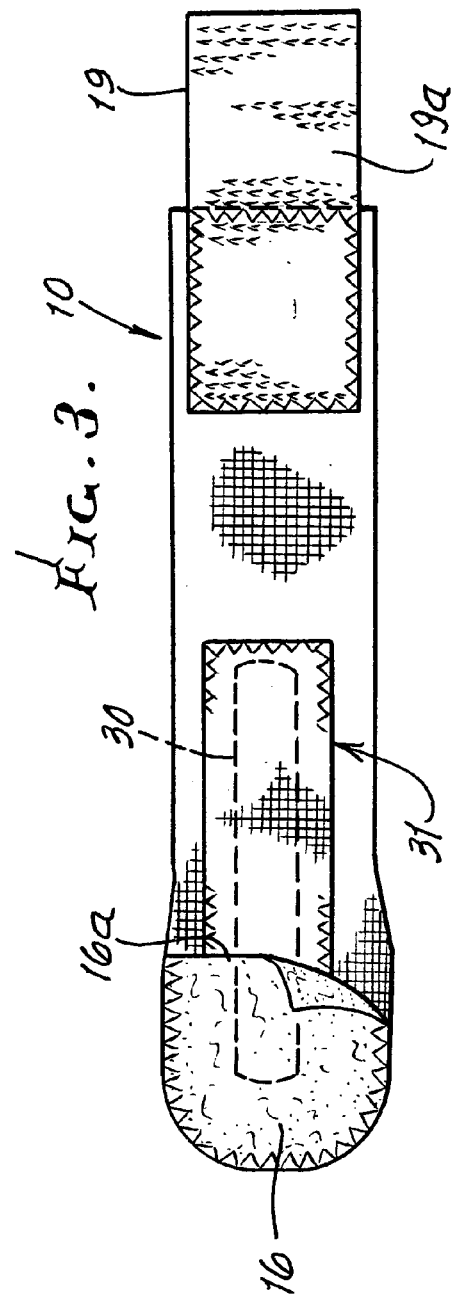

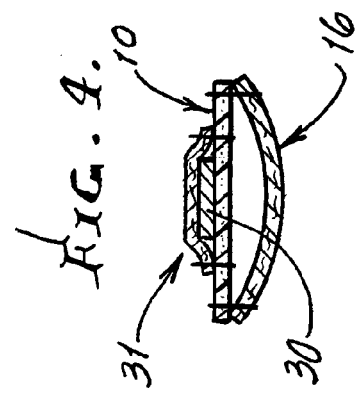
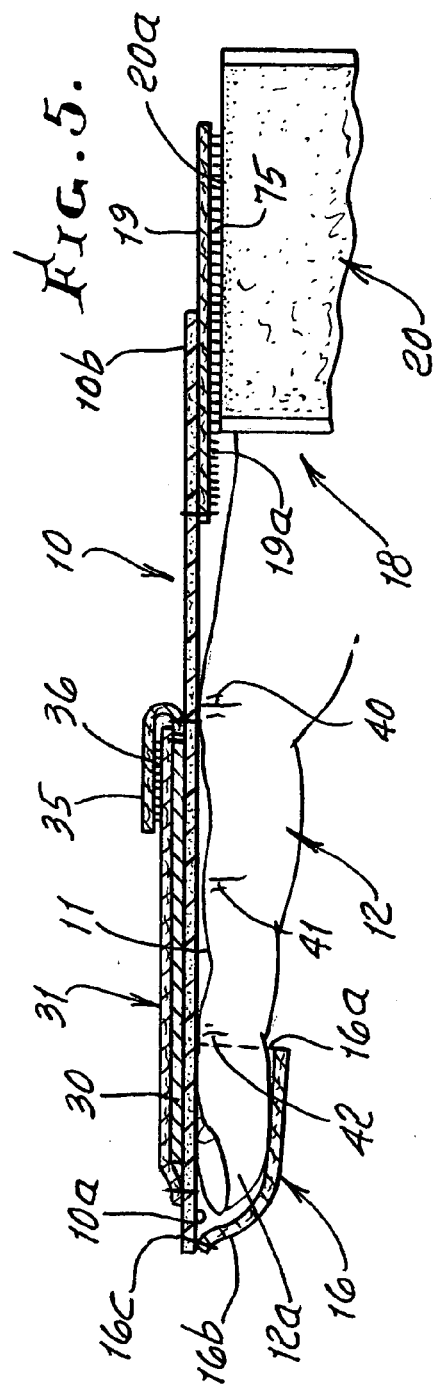
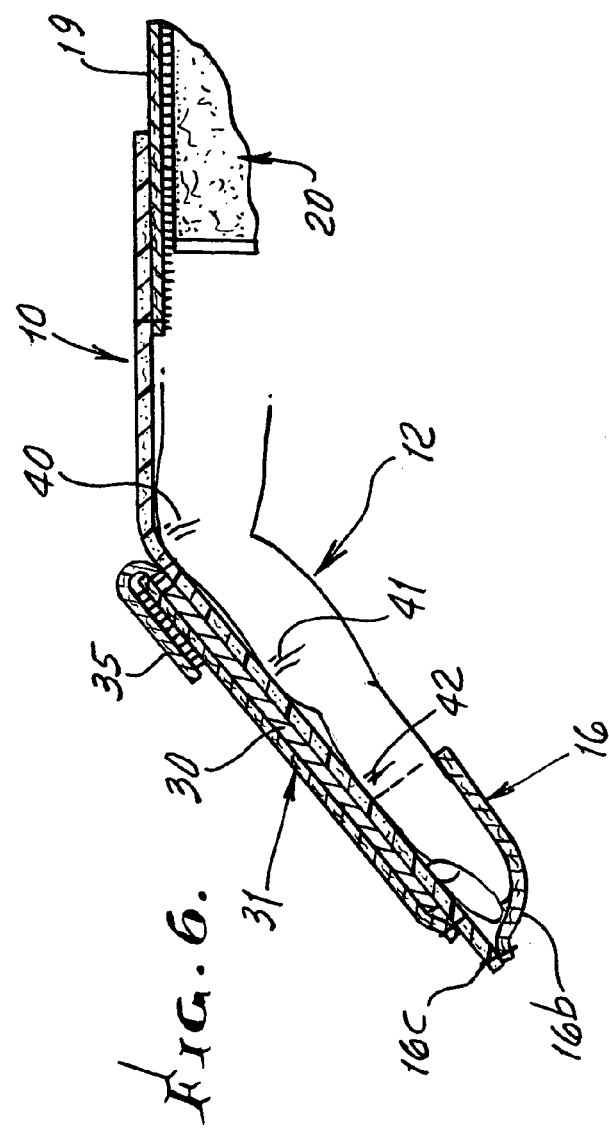

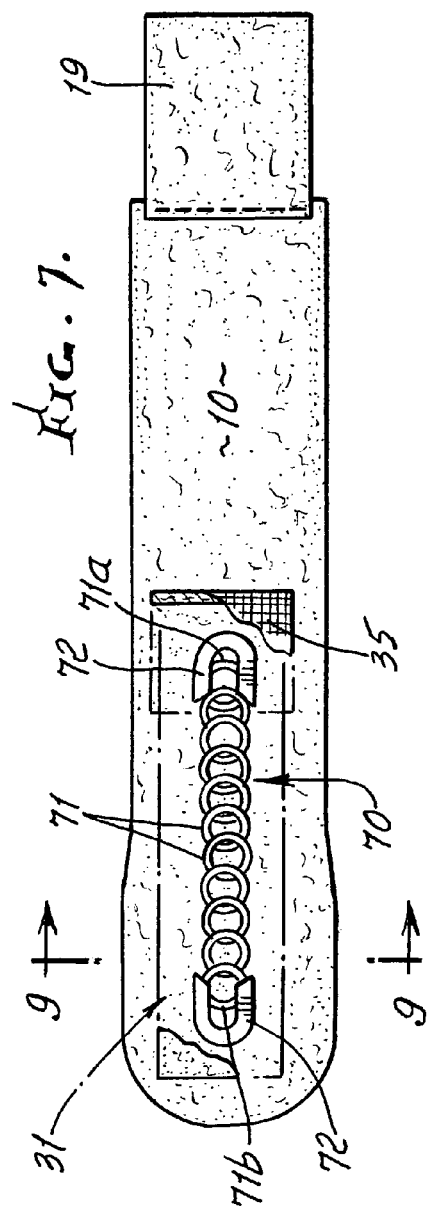
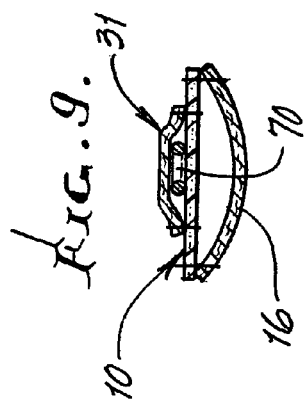
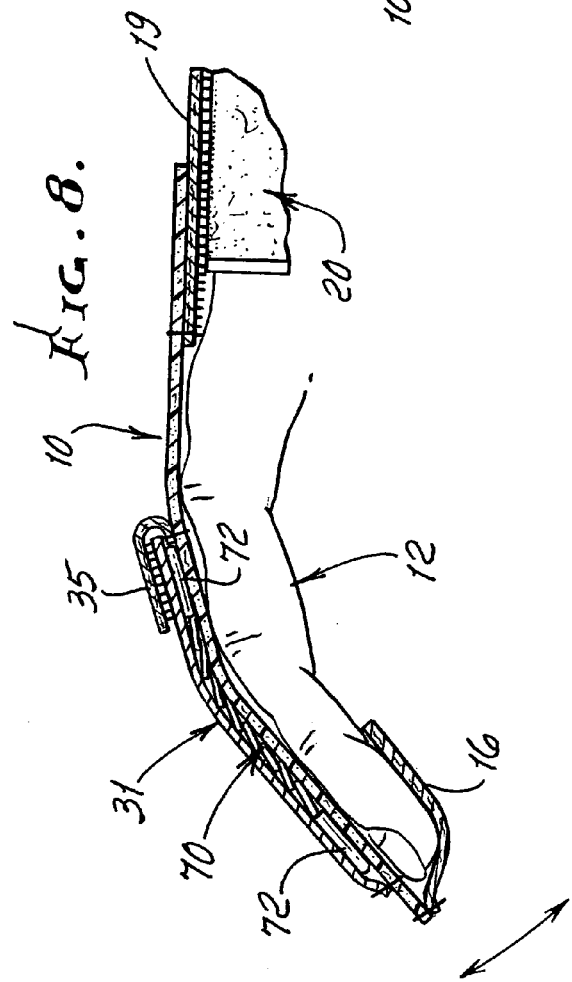

FINGER POSITIONER

BACKGROUND OF THE INVENTION

This invention relates generally to an easily applied, improved, digit splint which not only tends to retain the user's finger or thumb in an extended position, but which also accommodates temporary bending or flexing of the finger or thumb. There is need for a simple, effective splint having these multiple functions, as well as improvements in construction, configuration, and additional functions and results, as will appear.

SUMMARY OF THE INVENTION

It is a major object of the invention to provide an improved splint device meeting the above needs. Basically, the improved splint or positioner is operative to control the position of a finger or thumb of the user's hands, and comprises a) an elongated, flexible holder configured to extend along the upper side of the user's finger or thumb, b) a retainer carried by the holder to retain the tip of the user's finger or thumb, c) the holder adapted to be anchored, remotely from the retainer, endwise thereof, d) the holder configured to flex, thereby allowing bending of the finger or thumb, producing tensioning of the holder that resists such flexing.

Another object includes provision of a retainer that defines a receptacle to closely receive the tip of the user's finger or thumb.

A further object includes provision of a stiffener that extends generally parallel to the holder and acting to resist flexing of the holder. As will be seen, the holder typically includes flexible non-metallic material, that defines a pocket receiving the stiffener, the pocket being elongated and having an entrance via which the stiffener can be inserted endwise into the pocket. The stiffener may take the form of a lengthwise series of metallic loops which are interconnected to resiliently flex proximate finger joint locations allowing limited finger joint flexing. A flap may be provided to cover the pocket entrance, for blocking inadvertent stiffener exiting from or protrusion from the pocket, as during flexing of the holder with the user's finger or thumb.

As will be seen the stiffener typically includes at least one of the following:

i) an elongated flat spring,
ii) an elongated metallic strip,
iii) a series of relatively movable, interconnected metallic loops,
iv) an elongated resiliently yieldable element having a length to extend sidewise of at least two joints defined by the finger or thumb.

Yet another object of the invention is to provide a holder having an anchoring end portion remote from the retainer for the finger tip or thumb tip. That anchoring end portion typically includes hook or pile material adapted to press-connect to pile or hook material proximate the user's wrist.

A further object is to provide an anchoring sleeve to extend about the user's wrist, said pile or hook material located on said sleeve. In one desirable form of the invention the sleeve has a portion extending between the user's thumb and forefinger to aid in fitting the user's hand to the sleeve.

These and other objects and advantages of the invention, as well as the details of an illustrative embodiment, will be more fully understood from the following specification and drawings, in which:

DRAWING DESCRIPTION

FIG. 1 is a plan view of a user's hand showing application of finger positioner or splint;

FIG. 1a is a view similar to FIG. 1, but showing an alternative sleeve means for anchoring the positioner, to the wrist;

FIG. 2 is an enlarged top plan view of a preferred splint or positioner, as also seen in FIG. 1; and cut away to show interior construction;

FIG. 3 is a bottom plan view of the FIG. 2 splint;

FIG. 4 is a section taken on lines 4—4 of FIG. 2;

FIG. 5 is an enlarged section taken on lines 5—5 of FIG. 1;

FIG. 6 is a view like FIG. 5, but showing flexing of the holder, stiffener and finger;

FIG. 7 is a plan view of an alternative holder and showing a modified stiffener;

FIG. 8 is an elevation in section, showing the stiffener, holder and finger elements of FIG. 7, in flexed condition; and FIG. 9 is a section taken on lines 9—9 of FIG. 7.

DETAILED DESCRIPTION

Referring first to FIGS. 1 and 5, showing a preferred form of the invention, an elongated flexible holder 10 is configured to extend lengthwise along the upper side 11 of the user's finger 12. It can alternatively be extended along the upper side of a different finger, such as one of 13–15.

As seen in FIG. 5, a retainer 16 is carried by the holder 10 to receive and retain the tip 12a of the finger. The retainer has an open entrance or proximal end 16a, and a closed or distal end 16b, and it may be attached as at 16c to the underside 10a of the holder, near the distal end of the holder. The holder may take the form of a flap of flexible material.

The holder is adapted to be anchored, as to the user's hand upper side area 18, remotely from the retainer, i.e. endwise thereof. See for example the flap 19 attached to the holder, and projecting from the end lob of the holder for press-on attachment at 75 to the top surface area 20a of a wrist band or sleeve 20, wrapped about the user's wrist 21. The underside 19a of the flap 19 may carry hook or pile attachment material, for press-on attachment to pile or hook material at surface area 20a; and area 20a may be relatively wide or large in addition to the area 19a, for selective position attachment of 19a to 20a, i.e. in directions indicated by arrows 22 and 23. Wrap 20 has an end tab 20b that may have hook and pile attachment to the surface 20c. The holder is preferably tensioned, endwise, between 20 and the retainer or receptacle 16, which closely receives the user's finger tip.

FIG. 1a shows a modified anchoring means in the form of an elongated wrap 24, with an end portion 24a having hook and pile attachment to wrap outer surface 24c. Also, the wrap has an opening 25 to pass the user's thumb 26 to add to wrap anchoring to the user's wrist.

An additional feature includes the provision of a stiffener that extends generally endwise parallel to the holder, and acts to resist holder flexing. See for example stiffener 30 in FIG. 5 received in a pocket 31 on or defined by the holder. In the FIG. 1 and FIG. 5 examples, pocket 31 is elongated and attached to forward extent of the holder, as at end location 32, and side edge locations 33 and 34. The pocket has an open end 31a, which is typically closed by a retention flap 35 after the stiffener is inserted, endwise. Flap 35 is attached to 10, and may be folded back over the top of the pocket, and attached at 36, as by hook and pile material, whereby the stiffener is held endwise in position, relative to the holder, as the holder and stiffener are flexed in response to finger flexing, as in FIGS. 6 and 8.

In the form of the invention seen in FIGS. 5 and 6, the stiffener has the form of an elongated, flat, thin, straight, metallic strut or strip 30, extending lengthwise generally as and between finger joint area (knuckle) 40, and beyond finger joint area 42, i.e. bridging joint area 41. Accordingly, during finger flexing from knuckle 40, the holder, pocket, and stiffener hold the joint areas 41 and 42 in a straight or approximately straight line, i.e. joint areas 41 and 42 are not locally bent, as seen in FIG. 6. The stiffener strut may be in the form of a thin, flat spring, adapted to flex slightly, in FIG. 6 position. Holder 10 flexes at 10c in FIG. 6.

In the form of the invention seen in FIGS. 7 and 8, the stiffener includes a lengthwise series of metallic loops which are interconnected to resiliently flex proximate finger joint locations allowing limited finger joint flexing, as in FIG. 8. See for example the metallic loops 71 formed by the stiffener 70. The ends of the stiffener 70 are defined by the U-shaped receptacles 72 receiving end loops 71a and 71b.

We claim:

1. A positioner to control the position of a finger of the hand, comprising
    a) an elongated, flexible holder configured to extend along the upper side of the user's finger,
    b) a retainer carried by the holder to retain the tip of the user's finger,
    c) the holder adapted to be anchored, remotely from the retainer, endwise thereof,
    d) the holder configured to flex, thereby allowing bending of the finger, producing tensioning of the holder that resists such bending,
    (e) the retainer having a distal end attached to the underside of a distal end of the holder forming a substantially closed retaining zone to receive and retain the tip of the user's finger, the retainer further having an open proximal finger entrance end, both of said ends located at the underside of the elongated holder.

2. A positioner to control the position of a finger of the hand, comprising
    a) an elongated, flexible holder configured to extend along the upper side of the user's finger,
    b) a retainer carried by the holder to retain the tip of the user's finger,
    c) and including a stiffener extending generally parallel to the holder and acting to resist flexing of the holder,
    (e) the retainer having a distal end attached to the underside of a distal end of the holder forming a substantially closed retaining zone to receive and retain the tip of the user's finger, the retainer further having an open proximal finger entrance end, both of said ends located at the underside of the elongated holder.

3. The positioner of claim 1 including a stiffener extending generally parallel to the holder and acting to resist flexing of the holder.

4. The positioner of claim 3 wherein the holder includes flexible non-metallic material defining a pocket receiving the stiffener, at the upper side of the holder.

5. The positioner of claim 4 wherein the pocket and stiffener are elongated, the pocket having an entrance via which the stiffener can be inserted endwise into the pocket, to overlie the receptacle.

6. The positioner of claim 5 including a flap carried by the holder, and covering said pocket entrance, for blocking inadvertent stiffener exiting from or protrusion from the pocket, as during flexing of the holder with the user's finger.

7. The positioner of claim 3 wherein the stiffener includes at least one of the following:
    i) an elongated flat spring,
    ii) an elongated metallic strip,
    iii) a series of relatively movable, interconnected metallic loops,
    iv) an elongated resiliently yieldable element having a length to extend sidewise of at least two joints defined by the finger.

8. The positioner of claim 1 wherein the holder has an anchoring end portion remote from said retainer.

9. The positioner of claim 8 wherein said anchoring end portion includes hook or pile material adapted to removably press-connect to pile or hook material proximate the user's wrist.

10. The positioner of claim 9 including an anchoring sleeve to extend about the user's wrist, said pile or hook material located on said sleeve.

11. The positioner of claim 10 wherein said sleeve has a portion extending between the user's thumb and forefinger to aid in fitting the user's hand to the sleeve.

12. The positioner of claim 3 wherein the stiffener includes a lengthwise series of metallic loops which are interconnected to resiliently flex proximate finger joint locations allowing limited finger joint flexing.

13. The positioner of claim 2 wherein the stiffener includes a lengthwise series of metallic loops which are interconnected to resiliently flex allowing limited finger joint flexing.

14. The positioner of claim 2 wherein the holder includes flexible non-metallic material defining a pocket receiving the stiffener at the upper side of the holder.

15. The positioner of claim 14 wherein said pocket has length that substantially exceeds the length of said retainer.

16. The positioner of claim 15 wherein the pocket and stiffener are elongated, the pocket having an entrance via which the stiffener can be inserted endwise into the pocket, the length of the pocket substantially exceeding the length of said retainer, whereby said pocket entrance is located lengthwise of the pocket at a substantial distance from said proximal finger entrance end of the retainer.

17. The positioner of claim 16 including a flap carried by the holder, and covering said pocket entrance, for blocking inadvertent stiffener exiting from or protrusion from the pocket, as during flexing of the holder with the user's finger.

18. The positioner of claim 2 wherein the stiffener includes at least one of the following:
    i) an elongated flat spring,
    ii) an elongated metallic strip,
    iii) a series of relatively movable, interconnected metallic loops,
    iv) an elongated resiliently yieldable element having a length to extend sidewise of a joint defined by the finger.

19. The positioner of claim 2 including anchoring means carried by the holder.

20. The positioner of claim 19 wherein said anchoring means includes hook or pile material adapted to removably press-connect to pile or hook material associated with the holder.

* * * * *